(12) United States Patent
Hoffman et al.

(10) Patent No.: US 6,562,586 B1
(45) Date of Patent: May 13, 2003

(54) IN VITRO MODEL FOR HIV AND OTHER VIRAL DISEASES

(75) Inventors: Robert M. Hoffman, Lahoya, CA (US); Leonid B. Margolis, Bethesda, MD (US); Joshua Zimmerberg, Bethesda, MD (US); Svetlana Glushakova, Bethesda, MD (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/591,805

(22) Filed: Jun. 12, 2000

Related U.S. Application Data

(63) Continuation of application No. 08/885,242, filed on Jun. 30, 1997, now abandoned, which is a continuation of application No. 08/753,638, filed on Nov. 27, 1996, now abandoned.

(51) Int. Cl.$^7$ ............... C12Q 1/02; C12Q 1/06; C12Q 1/04; C12Q 1/18; C12P 39/00
(52) U.S. Cl. ............... 435/42; 435/5; 435/7.2; 435/7.24; 435/7.36; 435/34; 435/40.52; 435/239; 435/362; 435/366; 435/372; 435/374; 435/373; 435/32; 435/325
(58) Field of Search ............... 435/5, 325, 42, 435/7.21, 7.24, 7.36, 32, 34, 40.52, 239, 362, 366, 372, 374, 373

(56) References Cited

FOREIGN PATENT DOCUMENTS

WO    WO 97 45550 A    12/1997

OTHER PUBLICATIONS

Bonyhadi, M. et al., *AIDS Res. Hum. Retrovir*. (1995), vol. 11, pp. 1073–1080.
Freeman, A.E. and Hoffman, R.M., *Proc. Natl. Acad. Sci. USA* (1986), vol. 83, pp. 2694–2698.
Glushakova et al. *Nature Medicine* (1995), 1(12):1320–1322.
Glushakova et al. *Aids Research and Human Retroviruses* (1997), 13(6):461–471.
Hoffman, M.K. et al., *Nature* (1973), 243:408–410.
Hoffman, et al. *Journal of Immunological Methods* (1995), 179:37–49.
Lane, H.C. et al., *J. Exp. Med*. (1981), 154:1043–1057.
Leighton, J. et al., *Cancer Res*., (1957), vol. 17, pp. 929–941.
Leighton, J. et al., *National Cancer Inst*. (1951), vol. 12, pp. 545–561.
Margolis, M. et al. *Leukemia* (1994), 8(1):S163–165.
Margolis,M. et al. *Aids Research and Human Retroviruses* (1995), 11(6):697–704.
Mishell, R.I. et al., *Science* (1966), 153:1004–1006.
Rosensweig, M. et al., *Leukemia* (1994), vol. 8, Suppl. 1,S163–S165.

*Primary Examiner*—James Housel
*Assistant Examiner*—Bao Qun Li
(74) *Attorney, Agent, or Firm*—Morrison & Foerster LLP

(57) ABSTRACT

An in vitro model system for viral infection is comprised of a tissue block from adult tonsil or lymph node supported on a matrix which is flexible and porous and wherin the supported tissue block is cultured in a medium whose surface is congruent with the tissue block/matrix interface. The histoculture system can be used to screen for antiviral drugs and to monitor the course of viral diseases.

4 Claims, 1 Drawing Sheet

IN VITRO MODEL FOR HIV AND OTHER VIRAL DISEASES

CROSS-REFERENCE TO RELATED APPLICATIONS

This application is a continuation of U.S. patent application Ser. No. 08/885,242, filed Jun. 30, 1997, now abandoned, which is a continuation of and claims the benefit of the priority date of U.S. patent application Ser. No. 08/753,638, filed Nov. 27, 1996, now abandoned, under 35 U.S.C. § 120. The disclosure of the above-described applications are incorporated herein by reference in their entirety.

TECHNICAL FIELD

The invention relates to a model system for studying the progress of viral diseases and for assessing possible therapeutic and diagnostic protocols. Specifically, the invention concerns three-dimensional histocultures of adult lymph nodes and tonsils which provide substrates for infection, study, and discovering of new therapeutics and diagnostics.

BACKGROUND ART

The problem of providing a suitable model system for studying the progress of human immunodeficiency virus (HIV) and other viral diseases is well known. No in vivo model in animals for HIV, for example, is available at this time. Standard in vitro primary cell cultures do not mimic the full cellular repertoire within the tissues of an organism, and do not provide appropriate supracellular organization. Thus, it would be advantageous to have an in vitro model which more accurately mimics the behavior of the cells in the context of the organism.

Rosenszweig, M. et al., *Leukemia* (1994) 8:Suppl.1, S163–S165 and Bonyhadi, M. L. et al., *AIDS Res Hum Retrovir* (1995) 11:1073–1080 have cultured neonatal thymus as a tissue model for HIV pathogenesis. However, while these cultures support productive infection of HIV-1, they show thymocyte cytopathology and profile changes only after infection with macrophage-tropic but not lymphocyte-tropic strains. The histocultures of the present invention can be derived from adult tissues and are thus more representative of the progress of infection.

Various methods for culturing tumor cells in three-dimensional culture are known. Some of these are summarized in Leighton, J. et al., *Cancer Res* (1957) 17:929–941. A system for culturing human tumors in vitro in three dimensions was described by Freeman, A. E. and Hoffman, R. M., *Proc Natl Acad Sci USA* (1986) 83:2694–2698. Furtheore, a three-dimensional skin culture which could be used to evaluate toxicity and the effect of compounds on hair growth was described in WO92/15700 published Sep. 17, 1992.

Thus, applying techniques for three-dimensional histoculture, a model system for viral infection, particularly HIV infection, has been provided by the present invention.

DISCLOSURE OF THE INVENTION

The invention is directed to a histoculture system wherein lymph node or tonsil tissue is supported in a three-dimensional, structurally faithful system to serve as a model for viral infection, particularly HIV infection. Thus, in one aspect, the invention is directed to a histoculture system which is useful as an in vitro model for viral infection which system comprises a flexible macromolecular, porous matrix, and supported thereon, an integral macroscopic section of animal lymph node tissue or tonsil tissue, said matrix immersed in a suitable culture medium wherein the surface of the medium is approximately congruent with the interface between the tissue and the matrix. The section of tissue is then infected with an amount of virus effective to maintain growth of the virus.

In other aspects, the invention is directed to the in vitro histoculture system which is thus infected with a virus. In still other aspects, the invention is directed to a method to chart the progress of viral infection using the histoculture system of the invention and to methods to identify therapeutic compounds and protocols effective against the infection using the histoculture as a model, or as a diagnostic over the course of treatment administered to a subject.

The histoculture system of this invention can mount an immune response, as well as support infection by a virus, such as HIV. Such infection can inhibit the immune response, causing immunodeficiency in vitro.

MODES OF CARRYING OUT THE INVENTION

Figure 1:
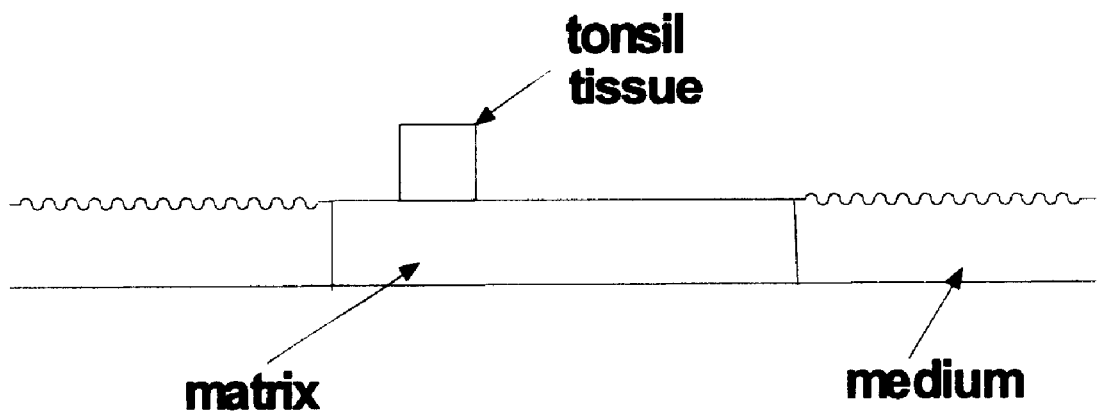
FIG. 1 is a schematic representation of the geometric configuration of the histocultures of the invention.

The method employs a histoculture system which permits growth of intact tissue samples in three dimensions while providing for adequate supply of nutrients and oxygen. The histoculture system employs a soft, porous matrix which is, preferably, comprised of extracellular material, such as collagen, polysaccharides, and the like. Suitable matrices are described in Leighton, J. (1957), Freeman (1986) and WO92/15700, all cited above, and all of which are incorporated herein by reference.

Briefly, the matrix is soft and flexible and may indent upon placement of the tissue such that the edges of the matrix may contact the vertical edges of the tissue. The matrix provides a trabecular structure with interstices suited for capillary action to deliver nutrients in the aqueous medium to the tissue supported on the matrix. While extracellular macromolecules are preferred, other materials that may be appropriate for the matrix include nylon, borosilicate, glass fiber, or polypropylene. However, preferred are solids comprising one or more organic molecules or molecular aggregates which are those produced and secreted by cells into the extracellular space and which serve, in vivo, as support, adhesive and framework for maintaining three-dimensional tissue organization and function. These molecules include high-molecular-weight proteins and glycoproteins, such as collagen, laminin, fibronectin and the like as well as complex polysaccharides.

Several commercially available materials can be used, including the gelatinized pork skin known as GELFOAM™, Upjohn Company, Kalamazoo, Mich.; a composition comprising laminin, collagen, proteoglycan and antactin such as MATRIGEL™, Collaborative Research, Inc., Bedford, Mass.; and a specialized collagen produced from pig skin by Health Design Industries, Rochester, N.Y. Other materials which can be used are homopolysaccharide sponges, such as those described by Leighton, J. et al., *J National Cancer Inst* (1951) 12:545–561. A combination of these materials can be used as well, such as a top layer of collagen containing gel and a bottom layer of homopolysaccharide sponge.

Other suitable matrices can be prepared de novo provided that they are capable of conducting medium to the supported material through capillary action and provide flexible support capable of maintaining medium approximately at the interface between the support and the tissue placed thereon.

The ratio of the tissue sample size to the support matrix dimensions is variable; preferably the matrix is of larger top supporting surface area than required to cover the entirety of the tissue sample. Multiple samples can be placed on the same matrix; it is preferred that they do not touch. The vertical dimension of the tissue is such that the nutnents of the medium can be transported through the tissue when the medium is maintained at approximately the lower surface of the tissue as placed on the support matrix.

In culture, the samples are placed on the matrix so that the interface between the tissue and the matrix coincides approximately with the surface of the medium. Thus, the matrix with the tissue sample is immersed in a volume of medium sufficient to contact the matrix but not to completely cover the tissue.

The support matrix is preferably pretreated with the culture medium before the tissue sample is placed. This serves to equilibrate the matrix with the medium. Generally, the matrix is cut to a predetermined size and soaked in the medium in a sterile container for a time sufficient to saturate and equilibrate the matrix, typically 4 hours at 37° C.

The media employed can vary, but a typical medium would comprise Eagle's Minimum Essential Medium (MEM) with 10% fetal bovine serum, 0.1 mM nonessential amino acids, and the antibiotics gentamicin (100 $\mu$g/ml) and cefotaxime (95 $\mu$g/ml). Other antibiotics may also be used.

The histocultures of the invention have been shown to support living tissue for extended periods and can be used as model systems for viral infection, particularly HIV infection. The progress of viral infection can be monitored in a variety of ways as is understood in the art. For example, at various time points after application of an effective amouiit virus to maintain viral growth, the tissues can be dissociated into single cells and the cells counted. Any method for counting the cells may be used, typically the cells are stained, either with an appropriate dye or with a labeled antibody. The cells can then be counted using any art-recognized techniques, for example, by flow cytometry.

Alternatively, or in addition, the progress of infection can be assessed by other means such as assays designed to monitor surface cell markers or assays designed to distinguish living from dead cells or assays which are relevant to aspects of intracellular metabolism.

The histoculture system can mount an immune response to an added antigen. This characteristic makes the system particularly valuable since infection by HIV may inhibit this immune response, and the ability of HIV infection to do so can be monitored. This provides an additional method for screening protocols and compositions useful in treating HIV, since the system can be tested in the presence and absence of the protocol or composition under conditions where an antigen has also been supplied and the effect of the protocol or composition on the development of immunodeficiency can be measured.

For use in drug and protocol testing, the histocultures, infected with the virus of interest, are cultured in the presence and absence of a candidate drug or protocol and the effect on the growth of the viral cells and on the health of viral-infected cells is assessed. Thus, if viral growth is impaired in the presence of the drug or protocol as compared to its absence, or if the cells maintain a healthy condition in the presence of the drug or protocol as compared to absence thereof, the drug or protocol is a successful candidate for viral treatment. This aspect is particularly important with respect to HIV, in view of the lack of suitable model systems for this virus. As stated above, this assay system can also be modified when HIV is the infective agent by monitoring the progress of immunodeficiency characterizing a response to an antigen in the presence of HIV infection. The effect of a candidate protocol or composition in controlling this immunodeficiency response can then be assessed. The histocultures may also be used to culture viruses of interest that may be difficult to passage in in vitro culture. In addition, the histocultures serve as diagnostic tools in assessing the progress of therapy. In this application, biopsies are removed from a patient being treated with a therapeutic regime and the effect on further growth in histoculture is assessed. This can be performed at various stages of the disease.

The following examples are intended to illustrate but not to limit the invention.

EXAMPLE 1

Preparation of Tonsil Histocultures

Human tonsils, surgically removed during therapeutic tonsillectomy, were dissected and blocks of tissue of about 1–2 mm in diameter were cultured on collagen sponge gel supports at a liquid/air interface for 10–26 days, as described by Freeman, A. E. et al., *Proc Natl Acad Sci USA* (1986) 83:2694–2698.

The histocultures maintained their morphology, and extended networks of follicular dendritic cells were found inside germinal centers by 3D reconstruction of confocal optical sections of histoculture blocks immunostained with FITC-labeled anti-CD21 antibodies. The cultures also produced IgG. Immunohistochemical analysis revealed well-defined germinal centers formed by B cells with T cells concentrated around them. Although in the first 24–36 hours, some depletion of lymphocytes occurred, all of the key elements of tissue architecture were preserved even in the fourth week in culture.

EXAMPLE 2

Virus Production

The histocultures prepared as in Example 1 were infected with HIV-1 at a multiplicity of infection (MOI) of 400–900 $TCID_{50}$ (median tissue culture infectious dose) per block. The strains used were as follows: LAV.04, (SI), a laboratory strain that induces syncytia in various cell lines and peripheral blood cells;

SF162, (NSI), a laboratory strain that does not induce syncytia;

Primary patient isolate 302144, (NSI), which does not induce syncytia; and

Primary patient isolate 302076, (NSI), which induces syncytia.

The latter two strains are from the NIH AIDS Research and Reference Reagent Program.

In all cases, viral particle production started between days 5 and 6 after infection. The amount of p24 measured by HIV-1 p24 antigen ELISA in the culture media increased exponentially until day 8, when it reached a plateau lasting until day 13. In culture media, virus infectious titers increased from undetectable levels on day 1 after infection, to $10^5$ $TCID_{50}$ $ml^{-1}$ on days 8–10 after infection. Productive viral infection was also confirmed by in situ hybridization with HIV RNA, using an antisense probe cocktail complementary to the entire HIV genome (sensitivity of about 20 copies of RNA) and by immunohistochemical detection of p24. By these criteria, no more than 3% of the tissue cells were productively infected.

No stimulation was required for the foregoing with either PHA or IL-2, in contrast to HIV infection in cultures of peripheral blood mononuclear cells.

Similar results were obtained when adult lymph nodes from recently deceased cadavers were substituted for tonsil tissue in the viral infection model.

EXAMPLE 3

Monitoring Progress of Infection

Tissue blocks from the same tonsil were divided in half. One half was inoculated with HIV. The response to infection was monitored by dissociating the tissue blocks into single cells at various time points, staining with fluorescent antibodies and counting cell populations using flow cytometry.

Isolate-dependent depletion of $CD4^-$ T cells in infected histocultures was found. The earliest decline was noticed on day 4 after infection. On days 10–13, when virus production for isolates equalized for all types of virus used and reached a plateau level, the $CD4^-/CD8^-$ ratio in tissues infected with SI types LAV or patient isolate 302076 was less than 4% of the uninfected control. In histocultures infected with wither NSI type SF162 or primary isolate 302144, the $CD4^-/CD8^-$ ratio was only 70% of the uninfected control. The $CD4^-/CD8^-$ ratio for blocks infected with the NSI isolate 302144 remained constant at day 20.

In addition to measuring relative cell populations, the absolute numbers of cell subsets in a block can be estimated by adding an internal standard number of fluorescent beads to the dissociated cell suspensions. On day 13 after infection with LAV, there was a total decline in the number of T lymphocytes ($CD3^-$) to 40±3% of control. There was no statistically significant change in the $CD8^-$ subset of cells. The observed decrease in the number of T cells was mainly due to depletion of the $CD4^-$ subset to 4±2% of control.

What is claimed is:

1. A method to identify a compound or protocol for the treatment of viral infection or virally-induced immunodeficiency, which method comprises maintaining a histoculture system in the presence and absence of said compound or protocol, monitoving the progress of viral infection or virally-induced immunodeficiency in the presence and absence of said compound or protocol; and comparing the progress of infection or virally-induced immunodeficiency in the presence and absence of said compound or protocol, whereby an inhibition of viral growth or improvement in immune status in the presence as opposed to the absence of said compound or protocol indicates effectiveness of the compound or protocol in inhibiting viral growth or ameliorating virally-induced immunodeficiency;

wherein said histoculture system comprises a flexible macromolecular, porous matrix having a trabecular structure, and supported thereon, an integral macroscopic section of animal lymph node tissue, said tissue having been infected with an amount of virus effective to maintain growth of the virus, said matrix immersed in a suitable culture medium wherein the surface of the medium is approximately congruent with the interface between the tissue and the matrix, whereby the tissue architecture is preserved.

2. The method of claim 1 wherein said virus is human immunodeficiency virus (HIV).

3. The method of claim 1, wherein the matrix is an extracellular macromolecular matrix.

4. The method of claim 3, wherein the matrix is collagen matrix.

* * * * *